US010772522B2

(12) United States Patent
Zadig

(10) Patent No.: US 10,772,522 B2
(45) Date of Patent: Sep. 15, 2020

(54) DISPOSABLE BIOMETRIC PATCH DEVICE

(71) Applicant: Vital Connect, Inc., Campbell, CA (US)

(72) Inventor: Stephen Zadig, Portola Valley, CA (US)

(73) Assignee: VITAL CONNECT, INC., Campbell, CA (US)

( * ) Notice: Subject to any disclaimer, the term of this patent is extended or adjusted under 35 U.S.C. 154(b) by 975 days.

(21) Appl. No.: 14/205,150

(22) Filed: Mar. 11, 2014

(65) Prior Publication Data

US 2014/0275932 A1    Sep. 18, 2014

Related U.S. Application Data

(60) Provisional application No. 61/777,900, filed on Mar. 12, 2013.

(51) Int. Cl.
*A61B 5/0408*  (2006.01)
*A61B 5/00*  (2006.01)
(Continued)

(52) U.S. Cl.
CPC ...... *A61B 5/04085* (2013.01); *A61B 5/02438* (2013.01); *A61B 5/0404* (2013.01); *A61B 5/6833* (2013.01); *A61B 5/0002* (2013.01); *A61B 5/01* (2013.01); *A61B 5/0205* (2013.01); *A61B 5/08* (2013.01); *A61B 5/0826* (2013.01); *A61B 5/1117* (2013.01); *A61B 5/4815* (2013.01); *A61B 5/4818* (2013.01);
(Continued)

(58) Field of Classification Search
CPC .............. A61B 5/0408; A61B 5/04085; A61B 5/04087; A61B 5/0492; A61B 2560/0412; A61B 2560/0443; A61B 2560/045; A61B 2560/0468; A61B 2560/0475; A61N 1/0492

See application file for complete search history.

(56) References Cited

U.S. PATENT DOCUMENTS 7,722,249 B2 *  5/2010  Kim ................. G01K 13/002
                                                            374/163
2003/0163287 A1 *  8/2003  Vock .................. A43B 3/0005
                                                            702/187
(Continued)

FOREIGN PATENT DOCUMENTS

CN     102740766 A    10/2012
EP        904038 B1    10/2001
(Continued)

OTHER PUBLICATIONS

Extended European Search Report dated Oct. 17, 2016.
International Search Report, dated Jul. 10, 2014.
Chinese Office Action dated Sep. 2, 2016.

*Primary Examiner* — Lee S Cohen
*Assistant Examiner* — Erin M Cardinal
(74) *Attorney, Agent, or Firm* — Brundidge & Stanger, P.C.

(57) ABSTRACT

A system and method for health monitoring are disclosed. The system includes a patch device and an electronic module coupled to the patch device. The method includes providing a patch device, coupling an electronic module to the patch device to provide a wearable device, and monitoring health of a user using the wearable device.

31 Claims, 3 Drawing Sheets

(51) Int. Cl.
  *A61B 5/0404*  (2006.01)
  *A61B 5/024*  (2006.01)
  *A61B 5/08*  (2006.01)
  *A61B 5/11*  (2006.01)
  *A61B 5/01*  (2006.01)
  *A61B 5/0205*  (2006.01)

(52) U.S. Cl.
  CPC . *A61B 2560/0285* (2013.01); *A61B 2560/045* (2013.01); *A61B 2562/0219* (2013.01)

(56) References Cited

U.S. PATENT DOCUMENTS

| | | |
|---|---|---|
| 2006/0015059 A1 | 1/2006 | Redding |
| 2006/0276700 A1 | 12/2006 | O'Neil et al. |
| 2007/0249946 A1* | 10/2007 | Kumar ................ A61B 5/0006 600/515 |
| 2008/0139953 A1* | 6/2008 | Baker ................ A61B 5/0006 600/509 |
| 2008/0275327 A1* | 11/2008 | Faarbaek ............ A61B 5/0002 600/382 |
| 2008/0300508 A1 | 12/2008 | Tomer |
| 2009/0076363 A1* | 3/2009 | Bly ................... A61B 5/0205 600/372 |
| 2011/0077497 A1 | 3/2011 | Oster et al. |
| 2011/0144470 A1 | 6/2011 | Mazar et al. |
| 2011/0279963 A1* | 11/2011 | Kumar ................ A61B 5/6833 361/679.31 |
| 2012/0071743 A1* | 3/2012 | Todorov .............. G06F 19/3481 600/372 |
| 2012/0088999 A1 | 4/2012 | Bishay et al. |
| 2012/0089037 A1* | 4/2012 | Bishay ................ A61B 5/0404 600/509 |
| 2012/0108920 A1 | 5/2012 | Bly et al. |
| 2013/0116533 A1* | 5/2013 | Lian .................... A61B 5/0006 600/391 |
| 2013/0116534 A1* | 5/2013 | Woo .................... A61B 5/0002 600/391 |
| 2013/0213147 A1* | 8/2013 | Rice .................... G01L 1/20 73/862.046 |
| 2013/0317333 A1* | 11/2013 | Yang ..................... A61B 5/00 600/372 |
| 2014/0206976 A1* | 7/2014 | Thompson ........... A61B 5/0006 600/391 |
| 2014/0206977 A1* | 7/2014 | Bahney ................ A61B 5/6833 600/391 |

FOREIGN PATENT DOCUMENTS

| | | | | |
|---|---|---|---|---|
| WO | WO 2012104657 A2 * | 8/2012 | ......... | A61B 5/04085 |
| WO | 2012125425 A2 | 9/2012 | | |
| WO | WO 2012149466 A2 * | 11/2012 | ......... | A61B 5/6833 |

* cited by examiner

DISPOSABLE BIOMETRIC PATCH DEVICE

CROSS-REFERENCE TO RELATED APPLICATION

This application claims benefit under 35 USC 119(e) of U.S. Provisional Patent Application No. 61/777,900, filed on Mar. 12, 2013, entitled "DISPOSABLE BIO-METRIC PATCH," which is incorporated herein by reference in its entirety.

FIELD OF THE INVENTION

The present invention relates to wearable sensor devices, and more particularly, to a disposable biometric patch device.

BACKGROUND

Wireless and wearable sensor devices are used to monitor the health of users. Many wearable devices are cumbersome for the user to use and therefore do not enable the automatic and continuous health monitoring of the users. Therefore, there is a strong need for a solution that overcomes the aforementioned issues. The present invention addresses such a need.

SUMMARY OF THE INVENTION

A system and method for health monitoring are disclosed. In a first aspect, the system includes a patch device and an electronic module coupled to the patch device.

In a second aspect, the method includes providing a patch device, coupling an electronic module to the patch device to provide a wearable device, and monitoring health of a user using the wearable device.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

The present invention relates to wearable sensor devices, and more particularly, to a disposable biometric patch device. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Wireless and wearable sensor devices can be utilized for the remote, automated, and continuous health monitoring of users/patients. A method and system in accordance with the present invention provides a wireless, portable, and wearable sensor device ("wearable device") that comprises a disposable biometric device that is in a patch form factor and a reusable electronic module that is coupled/attached to the disposable biometric device. In another embodiment, the wearable device comprises one disposable component that includes both the biometric device and the electronic module. The wearable device is attached to a user to automatically and continuously detect a plurality of health related and physiological signals including but not limited to ECG, respiratory, and acceleration signals.

In one embodiment, the disposable biometric device component of the wearable device is an ultra low cost and fully disposable biometric patch that is attached to the user's skin and used in conjunction with the electronic module to detect, record, and analyze a plurality of health related metrics including but not limited to the user's heart rate (beats per minute), ECG wave form, respiration, skin temperature, activity (e.g. number of steps), posture (e.g. standing, sitting, supine, or body angle), falls detection, stress determinations, sleep quality, sleep apnea detection, and apnea-hypopnea index (AHI) calculation.

In this embodiment, the wearable device captures the plurality of health related metrics utilizing a plurality of sensors including but not limited to a single lead ECG, accelerometer, and altimeter. The detected plurality of health related metrics are then processed and analyzed using either integrated processors and algorithms of the wearable device (e.g. the reusable electronic module) or an external processing device (e.g. smartphone device, cloud-based server network).

Figure 1:
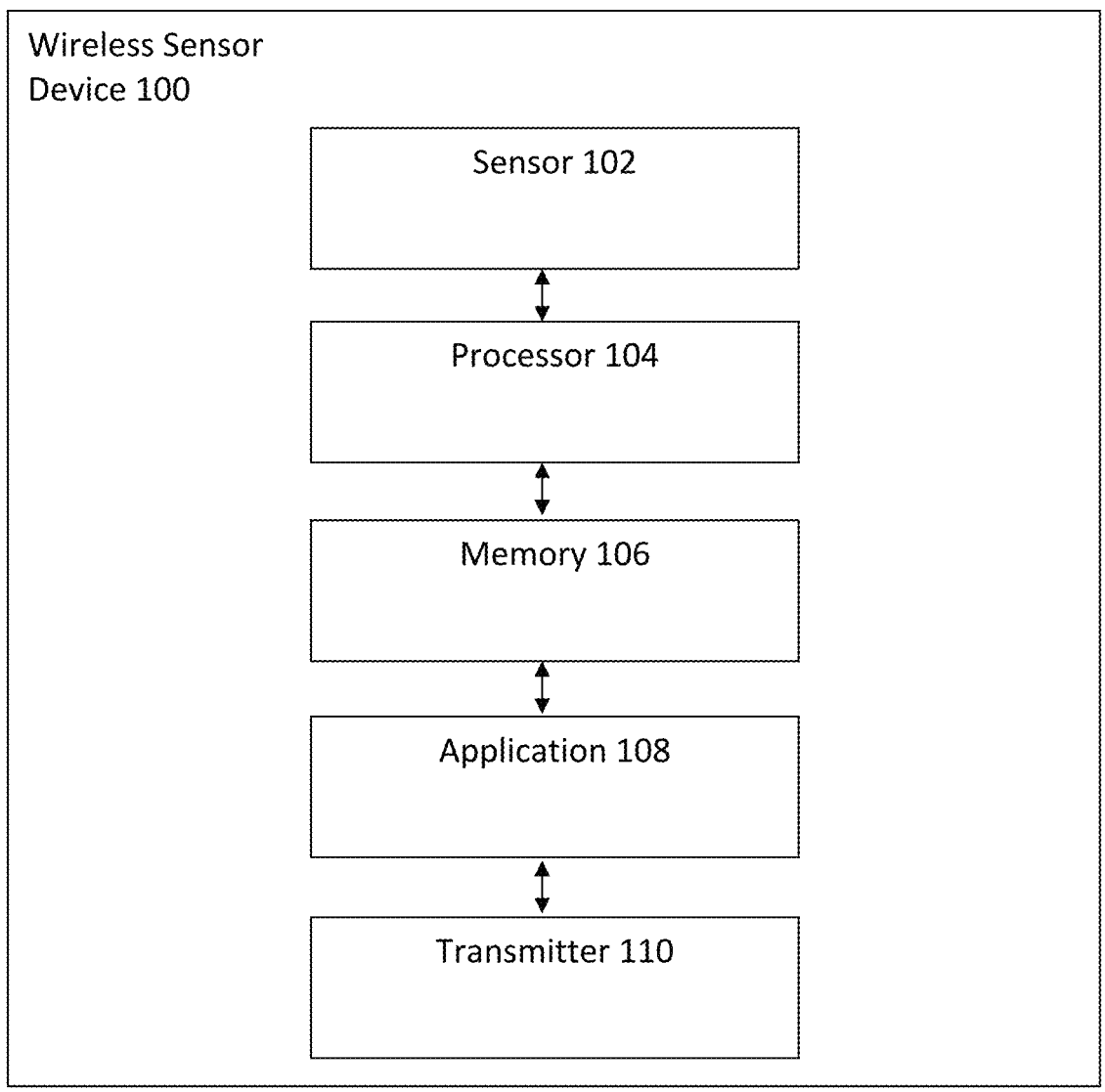
FIG. 1 illustrates a wireless sensor device for health monitoring in accordance with an embodiment.

FIG. 1 illustrates a wireless sensor device 100 for health monitoring in accordance with an embodiment. The wireless sensor device 100 or wearable device includes a sensor 102, a processor 104 coupled to the sensor 102, a memory 106 coupled to the processor 104, an application 108 coupled to the memory 106, and a transmitter 110 coupled to the application 108.

In one embodiment, the wireless sensor device 100 is attached to a user to detect various physiological signals/data via the sensor 102. The sensor 102 obtains data from the user which is transmitted to the memory 106 and in turn to the application 108 via the processor 104. The processor 104 executes the application 108 to process and obtain information regarding the user's health. The information is transmitted to the transmitter 110 and in turn relayed to another user or device for further processing, analysis, and storage. In another embodiment, the transmitter 110 transmits the various detected physiological signals in raw form to a remote device/server (e.g. smartphone, cloud-based server) for processing, analysis, and storage.

In one embodiment, the sensor 102 is any of a microelectromechanical system (MEMS) tri-axial accelerometer and an embedded sensor with electrodes and the processor 104 is any of a microprocessor and a reusable electronic module. One of ordinary skill in the art readily recognizes that a variety of devices can be utilized for the sensor 102, the processor 104, the memory 106, the application 108, and the transmitter 110 and that would be within the spirit and scope of the present invention.

Additionally, one of ordinary skill in the art readily recognizes that a variety of wireless sensor devices can be utilized including but not limited to wearable devices, a wireless sensor device in a patch form-factor, the Vital Connect HealthPatch™ wearable device, tri-axial accelerometers, uni-axial accelerometers, bi-axial accelerometers, gyroscopes, and pressure sensors and that would be within the spirit and scope of the present invention.

To describe the features of the present invention in more detail, refer now to the following description in conjunction with the accompanying Figures.

Figure 2:
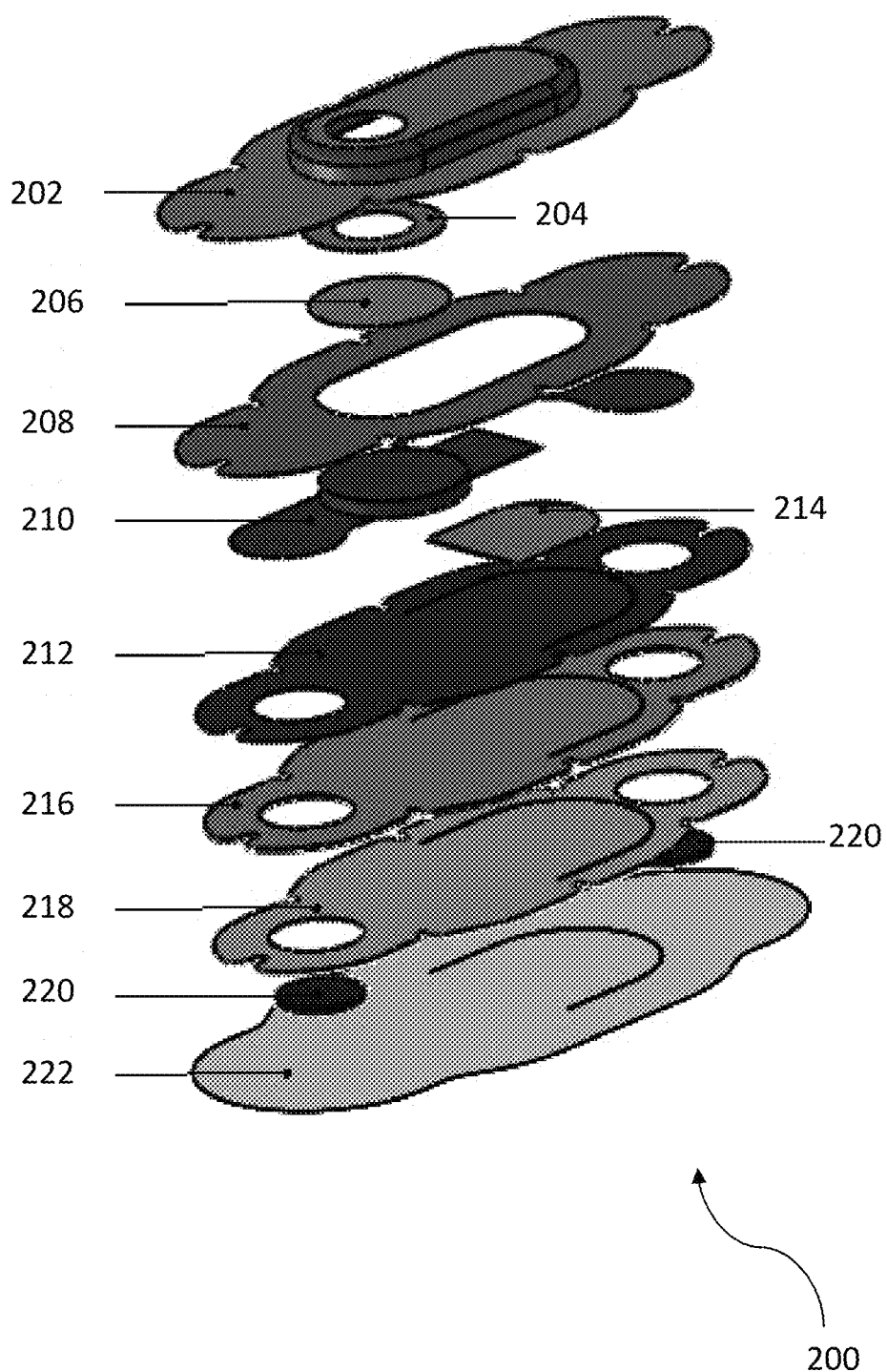
FIG. 2 illustrates a disposable patch device of a wearable device for health monitoring in accordance with an embodiment.

FIG. 2 illustrates a disposable patch device 200 of a wearable device for health monitoring in accordance with an embodiment. The disposable patch device 200 is a component of the wearable device that is utilized in conjunction with the reusable electronic module to monitor the health of users/patients.

In FIG. 2, the disposable patch device 200 comprises a plurality of layers including a top layer 202, a disk layer 204 coupled to the top layer 202 via an adhesive disk layer 206, an adhesive intermediate layer 208 coupled to the top layer 202, a sub-assembly layer 210 coupled to the adhesive intermediate layer 208, an adhesive die cut layer 212 coupled to the adhesive intermediate layer 208, a flap layer 214 coupled to the adhesive die cut layer 212, a foam layer 216 coupled to the adhesive die cut layer 212, an adhesive bottom layer 218 coupled to the foam layer 216, electrode gels 220 coupled to the adhesive bottom layer 218, and a release liner 222 coupled to the adhesive bottom layer 218.

In one embodiment, the top layer 202 includes a first foundation layer with two circular areas on opposite ends of the first foundation layer and a chamber area coupled to the first foundation layer (e.g. residing on top of the first foundation layer). In one embodiment, the top layer 202 comprises any of closed cell foam and closed cell polyethylene foam. In this embodiment, the closed cell foam and the closed cell polyethylene foam are coated with an anti-static material/film to reduce tribo-electric charging. In one embodiment, the anti-static material/film is Clevios PEDOT. The top layer 202 is formed to create the chamber area that can house a reusable electronic module and a battery. In one embodiment, the top layer 202 is thermo formed. In one embodiment, a hole is die cut in the chamber area of the top layer 202 to accommodate any of units 204-222.

In one embodiment, the disk layer 204 is a breathable membrane that is die cut. An adhesive disk layer 206 is coupled to the disk layer 204 to enable the disk layer 204 to be coupled/attached to the top layer 202 in a manner such that a waterproof bond is created. In one embodiment, the breathable membrane is any of a Versapor material including but not limited to Versapor 200R and a Tyvek synthetic material including but not limited to Tyvek 1059B and the adhesive disk layer 206 is any of a transfer adhesive and a double-sided adhesive. The breathable membrane allows the diffusion of oxygen but keeps water from penetrating the disposable patch device 200 to a certain depth and for a certain duration. In one embodiment, the depth is 3 feet and the duration is 1 hour.

In one embodiment, the adhesive intermediate layer 208 is applied to the top layer 202 to provide a sealing adhesive for the attachment of subsequent layers 210-222 and the formation of an additional waterproof bond. In one embodiment, the adhesive intermediate layer 208 is any of an intermediate transfer adhesive layer and an intermediate double sided die cut adhesive layer.

In one embodiment, the sub-assembly layer 210 comprises an electronic flex circuit that is fabricated to allow for the housing of at least two electrodes and the creation of an ECG device, the attachment of a battery, and integrated circuits that serve as a connector for the attachment of the reusable electronic module. In one embodiment, the electronic flex circuit is copper clad, the ECG device is single lead and is created by coating NiAu electrodes with Ag/AgCl, the battery is a Zinc-air battery that attaches to NiAu pads of the electronic flex circuit, and the integrated circuits include but are not limited to a signal line SIM card 8 lead connector with attached stiffener. The sub-assembly layer 210 is attached to the adhesive intermediate layer 208 such that the battery, the electronic flex circuit, and the connector are aligned and housed within the chamber area of the top layer 202.

In one embodiment, the adhesive die cut layer 212 is any of a transfer adhesive and a double sided adhesive. The adhesive die cut layer 212 is coupled (e.g. laminated) to the foam layer 216 thereby creating a selective waterproof seal over the sub-assembly layer 210. In one embodiment, the foam layer 216 is any of closed cell foam and polyethylene foam. In one embodiment, a sealable flap is cut within both the die cut layer 212 and the foam layer 216 to enable the insertion and attachment of the reusable electronic module to the disposable patch device 200. In one embodiment, two circular holes are die cut within both the adhesive die cut layer 212 and the foam layer 216 to enable access to and attachment of the ECG electrodes. The flap layer 214 is placed on the sealable flap to prevent the adhesive die cut layer 212 from sticking to the reusable electronic module once inserted and sealed within the disposable patch device 200 while allowing for a seal along the outer edges of the sealable flap.

In one embodiment, the adhesive bottom layer 218 is coupled to the bottom of the foam layer 216. The adhesive bottom layer 218 is skin side and thus interacts with the user's skin. As a result, the adhesive bottom layer 218 comprises a plurality of materials that are selected to meet the needs of the specific user's sensitivity, usage requirements (e.g. passive, active, etc.), and skin type (e.g. young, healthy, aged, fragile, sensitive, etc.). In one embodiment, a sealable flap is cut within the adhesive bottom layer 218 to enable the insertion and attachment of the reusable electronic module to the disposable patch device 200. In one embodiment, two circular holes are die cut within the adhesive bottom layer 218 to enable access to and attachment of the at least two electrodes of the sub-assembly layer 210 via the electrode gels 220.

In one embodiment, the electrode gels 220 are applied to the exposed at least two electrodes of the sub-assembly layer 210 in order to be in contact with the user's skin. The two electrodes of the sub-assembly layer 210 are exposed and in contact with the user's skin because of the access fostered via the two circular holes that are die cut in the adhesive die cut layer 212, the foam layer 216, and the adhesive bottom layer 218. In one embodiment, the adhesive bottom layer 218 is customized in size and shape (e.g. undersized, oversized, etc.) to enable combinations of additional adhesives or the presence of areas that do not have any adhesives. In one embodiment, the adhesive bottom layer 218 includes an exposed edge that aggressively contacts the user's skin to create a water resistant edge.

In one embodiment, the adhesive bottom layer 218 of the device 200 comprises a plurality of stacked adhesive layers that enable the user/patient/wearer of the disposable patch device 200 to remove the disposable patch device 200 and expose a new layer of the plurality of stacked adhesive layers multiple times during usage of the disposable patch device 200. Each of the plurality of stacked adhesive layers are removed via the use of tabs that are integrated into each of the plurality of stacked adhesive layers thereby extending the life of the disposable device 200. In one embodiment, the life of the disposable device 200 ranges from a few seconds to one year as applicable.

In one embodiment, the electrode gels 220 are circular die cut gel tabs of ECG grade hydrogel that are applied through the die cut layer 212, the foam layer 216, and the adhesive bottom layer 218 and placed in contact with exposed electrodes of the sub-assembly layer 210. In one embodiment, the total thickness of the electrode gels 220 are any of at least 0.25 millimeters (mm) to 0.01 inches above the skin contact surface of the foam layer 216.

In one embodiment, a sealable flap is cut within the release liner 222 to enable the insertion and attachment of the reusable electronic module to the disposable patch device 200. The release liner 222 is aligned and coupled to the adhesive bottom layer 218 and is in contact with the electrode gels 220. The release liner 222 is removed and discarded by the user of the wearable device to enable the adhesive bottom layer 218 and the at least two electrodes of the sub-assembly layer 210 to come in contact with the user's skin via the two circular holes that are die cut within each of the adhesive die cut layer 212, the foam layer 216, and the adhesive bottom layer 218. The release liner 222 serves as a protective bottom layer that protects the adhesive bottom layer 218 and electrode gels 220 from drying and contamination before the disposable patch device 200 is used and placed in contact with the user's skin.

After completing the assembly of the disposable patch device 200, the disposable patch device 200 is die cut to create a final shape and to trim off excess materials or singulation if gang assembled. In one embodiment, a plurality of notches are die cut through all of the layers of the disposable patch device 200. In one embodiment, the plurality of notches are die cut around the perimeter of the disposable patch device 200 and are separated by any of symmetrical spacing and predetermined spacing requirements (e.g. 8 notches per disposable patch device 200). The plurality of notches allow the disposable patch device 200 to adhere and to conform to the curvatures and muscle/tissue movement thereby reducing mechanical stress on the overall wearable device, the disposable patch device 200, the electronic module, and related adhesives. This enables the wearable device to be in contact with the user's skin for prolonged and/or optimized periods of time.

In one embodiment, the disposable patch device 200 is finalized for packaging and long term storage in a pouch comprising a mylar bottom layer and a clear top PET layer that is hermetically heat sealed to impede exposure to air which would reduce battery life and dry out the electrode gels 220. In one embodiment, the mylar bottom layer is any of an alumnized mylar bottom layer and a metalized mylar bottom layer. In one embodiment, the clear top PET layer is a layer that has been formulated to allow very low diffusion rates of O2 so that the battery (e.g. Zinc-air battery) that is utilized within the sub-assembly layer 210 can be stored for up to one year without significant capacity loss.

Figure 3:
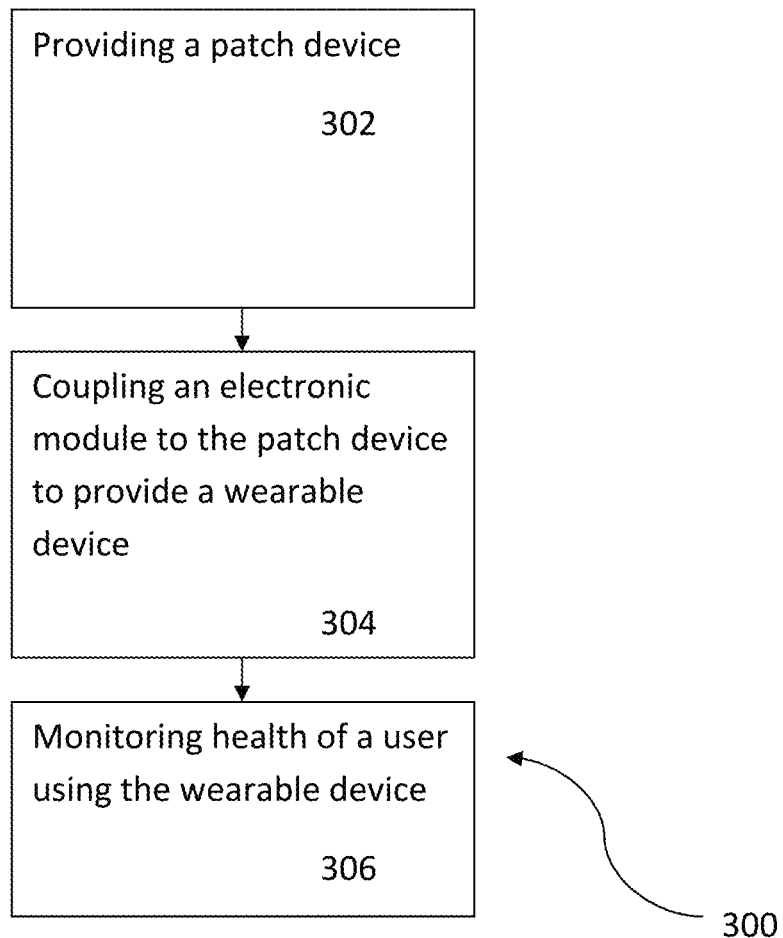
FIG. 3 illustrates a method for health monitoring in accordance with an embodiment.

FIG. 3 illustrates a method 300 for health monitoring in accordance with an embodiment. The method 300 includes providing a patch device, via step 302, coupling an electronic module to the patch device to provide a wearable device, via step 304, and monitoring health of a user using the wearable device, via step 306. In one embodiment, the patch device is disposable and the electronic module is reusable.

In one embodiment, the reusable electronic module is coupled by inserting the reusable electronic module into the disposable patch device that includes circuit connectors to receive the reusable electronic module. In one embodiment, the providing step 302 further comprises manufacturing and assembling the disposable patch device in accordance with the layer descriptions and architecture of the disposable patch device 200 that are described by FIG. 2.

As above described, a method and system in accordance with the present invention provide a wearable device that includes a disposable patch device component and a reusable electronic module component. The disposable patch device component comprises a plurality of layers that house various components (e.g. single lead ECG) and enable the coupling/insertion of the reusable electronic module. The flexible and layered architecture of the disposable patch device extends the usage and customizability of the device and can be manufactured at very high volumes and at very low costs. The disposable patch device is water resistance and can pass standards for water ingress such as IPX4 and IPX7.

By utilizing advanced adhesives, the disposable patch device is comfortably worn by the user with little or no skin irritation for long periods of time (e.g. no irritation for up to 7 days) and the removal stress is minimized to avoid damaging or discomforting the skin tissue. The flexibility of the disposable patch device maintains a high quality single lead ECG electrode to contact with the user's body/skin with very low static noise and motion artifacts. Additionally, the disposable patch device is unobtrusive and comfortable to a point that the user is unaware that it is attached to the body while the user is conducting active activities (e.g. walking, running), passive activities (e.g. watching television), and sleeping.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A system for health monitoring, the system comprising:
a patch device; and
an electronic module removably coupled to the patch device;
wherein the patch device further comprises:
 a top layer;
 a sub-assembly layer coupled to the top layer, wherein the sub-assembly layer comprises an electronic flex circuit, and wherein the electronic flex circuit includes at least two electrodes, a battery, and integrated connector circuits for attachment of the electronic module; and
 a bottom layer coupled to the sub-assembly layer, and
wherein the patch device includes a sealable flap including an adhesive die cut layer and a foam layer, and
a flap layer between the electronic module and the sealable flap, wherein the flap layer is part of the patch device and prevents the adhesive die cut layer from sticking to the electronic module while allowing for a seal along outer edges of the sealable flap.

2. The system of claim 1, wherein the patch device is disposable and the electronic module is reusable.

3. The system of claim 1, wherein the top layer comprises a first layer with two circular areas on opposite ends of the first layer and a chamber area that resides on top of the first layer to house the electronic module.

4. The system of claim 1, wherein the top layer comprises any of: closed cell foam, polyethylene foam, or a combination thereof, further wherein the top layer is coated with an anti-static material.

5. The system of claim 1, further comprising:
a first intermediate layer that is coupled between the top layer and the sub-assembly layer.

6. The system of claim 5, wherein the first intermediate layer comprises a disk layer, an adhesive disk layer coupled to the disk layer, and an adhesive intermediate layer to create a waterproof bond for the patch device.

7. The system of claim 5, further comprising:
a second intermediate layer that is coupled between the sub-assembly layer and the bottom layer.

8. The system of claim 7, wherein the second intermediate layer comprises the adhesive die cut layer and the foam layer coupled to the adhesive die cut layer to create a waterproof seal over the sub-assembly layer.

9. The system of claim 8, wherein the foam layer comprises any of: closed cell foam, polyethylene foam, or a combination thereof.

10. The system of claim 8, wherein both the adhesive die cut layer and the foam layer include two circular holes.

11. The system of claim 10, wherein the bottom layer comprises an adhesive bottom layer and a release liner coupled to the adhesive bottom layer.

12. The system of claim 11, wherein the adhesive bottom layer includes both the sealable flap and the two circular holes, further wherein the release liner only includes the sealable flap.

13. The system of claim 11, wherein the adhesive bottom layer comprises a plurality of stacked adhesive layers that are each separately removable via a corresponding tab integrated into each of the plurality of stacked adhesive layers.

14. The system of claim 1, further comprising:
at least two electrode gels that are coupled to the at least two electrodes of the sub-assembly layer via two circular holes.

15. The system of claim 14, further comprising:
a plurality of notches cut into the patch device to enhance adherence and conformance.

16. A system for health monitoring, the system comprising:
a patch device; and
an electronic module coupled to the patch device,
wherein the patch device further comprises:
a top layer;
a sub-assembly layer coupled to the top layer, wherein the sub-assembly layer comprises an electronic flex circuit, and wherein the electronic flex circuit includes at least two electrodes, a battery, and integrated connector circuits for attachment of the electronic module;
a first intermediate layer that is coupled to the top layer and the sub-assembly layer to form a housing for the electronic module, wherein the first intermediate layer comprises a disk layer, an adhesive disk layer coupled to the disk layer, and an adhesive intermediate layer to create a waterproof bond for the disposable patch device, wherein the disk layer comprises a breathable membrane, wherein the breathable membrane allows diffusion of oxygen but keeps water from penetrating the disposable patch device to a certain depth and for a certain duration; and
a bottom layer coupled to the sub-assembly layer.

17. The system of claim 16, wherein the patch device is disposable and the electronic module is reusable.

18. The system of claim 16, wherein the top layer comprises a first layer with two circular areas on opposite ends of the first layer and a chamber area that resides on top of the first layer to house the electronic module.

19. The system of claim 16, wherein the top layer comprises any of: closed cell foam, polyethylene foam, or a combination thereof, further wherein the top layer is coated with an anti-static material.

20. The system of claim 16, further comprising:
a second intermediate layer that is coupled between the sub-assembly layer and the bottom layer.

21. The system of claim 20, wherein the second intermediate layer comprises an adhesive die cut layer and a foam layer coupled to the adhesive die cut layer to create a waterproof seal over the sub-assembly layer.

22. The system of claim 21, wherein the foam layer comprises any of: closed cell foam, polyethylene foam, or a combination thereof.

23. The system of claim 21, wherein both the adhesive die cut layer and the foam layer include a sealable flap and two circular holes.

24. The system of claim 23, further comprising:
a flap layer coupled to the sealable flap of the adhesive die cut layer to prevent the adhesive die cut layer from sticking to the electronic module.

25. The system of claim 23, wherein the bottom layer comprises an adhesive bottom layer and a release liner coupled to the adhesive bottom layer.

26. The system of claim 25, wherein the adhesive bottom layer includes both the sealable flap and the two circular holes, further wherein the release liner only includes the sealable flap.

27. The system of claim 25, wherein the adhesive bottom layer comprises a plurality of stacked adhesive layers that are each separately removed via a corresponding tab.

28. The system of claim 16, further comprising:
at least two electrode gels that are coupled to the at least two electrodes of the sub-assembly layer via two circular holes.

29. The system of claim 28, further comprising:
a plurality of notches cut into the patch device to enhance adherence and conformance.

30. A method for health monitoring, the method comprising:
providing a system comprising:
a patch device; and
an electronic module removably coupled to the patch device to provide a wearable device,
wherein the patch device further comprises:
a top layer;
a sub-assembly layer coupled to the top layer, wherein the sub-assembly layer comprises an electronic flex circuit, and wherein the electronic flex circuit includes at least two electrodes, a battery, and integrated connector circuits for attachment of the electronic module; and
a bottom layer coupled to the sub-assembly layer, and
wherein the patch device includes a sealable flap including an adhesive die cut layer and a foam layer, and
a flap layer between the electronic module and the sealable flap, wherein the flap layer is part of the patch device and prevents the adhesive die cut layer from sticking to the electronic module while allowing for a seal along outer edges of the sealable flap; and monitoring health of a user using the wearable device.

31. A method for health monitoring, the method comprising:
- providing a system comprising:
  - a patch device; and
  - an electronic module coupled to the patch device to provide a wearable device, wherein the patch device further comprises:
    - a top layer;
    - a sub-assembly layer coupled to the top layer, wherein the sub-assembly layer comprises an electronic flex circuit, and wherein the electronic flex circuit includes at least two electrodes, a battery, and integrated connector circuits for attachment of the electronic module;
    - a first intermediate layer that is coupled to the top layer and the sub-assembly layer to form a housing for the electronic module, wherein the first intermediate layer comprises a disk layer, an adhesive disk layer coupled to the disk layer, and an adhesive intermediate layer to create a waterproof bond for the disposable patch device, wherein the disk layer comprises a breathable membrane, wherein the breathable membrane allows diffusion of oxygen but keeps water from penetrating the disposable patch device to a certain depth and for a certain duration; and
    - a bottom layer coupled to the sub-assembly layer; and monitoring health of a user using the wearable device.

* * * * *